(12) United States Patent
Kandori et al.

(10) Patent No.: US 10,588,521 B2
(45) Date of Patent: Mar. 17, 2020

(54) SPHYGMOMANOMETER SYSTEM

(71) Applicant: HITACHI, LTD., Tokyo (JP)

(72) Inventors: Akihiko Kandori, Tokyo (JP); Yuko Sano, Tokyo (JP); Toshio Tsuji, Hiroshima (JP); Harutoyo Hirano, Hiroshima (JP)

(73) Assignee: Hitachi, Ltd., Tokyo (JP)

( * ) Notice: Subject to any disclaimer, the term of this patent is extended or adjusted under 35 U.S.C. 154(b) by 550 days.

(21) Appl. No.: 14/902,916

(22) PCT Filed: Jul. 10, 2013

(86) PCT No.: PCT/JP2013/068882
§ 371 (c)(1),
(2) Date: Jan. 5, 2016

(87) PCT Pub. No.: WO2015/004754
PCT Pub. Date: Jan. 15, 2015

(65) Prior Publication Data
US 2016/0150984 A1  Jun. 2, 2016

(51) Int. Cl.
*A61B 5/022* (2006.01)
*A61B 5/021* (2006.01)
*A61B 5/00* (2006.01)

(52) U.S. Cl.
CPC ...... *A61B 5/02241* (2013.01); *A61B 5/02116* (2013.01); *A61B 5/02141* (2013.01);
(Continued)

(58) Field of Classification Search
None
See application file for complete search history.

(56) References Cited

U.S. PATENT DOCUMENTS 4,802,488 A * 2/1989 Eckerle ............ A61B 5/02007
600/485
5,941,828 A * 8/1999 Archibald .......... A61B 5/02116
600/494
(Continued)

FOREIGN PATENT DOCUMENTS

JP   H02-261421 A   10/1990
JP   H10-151117 A    6/1998
(Continued)

OTHER PUBLICATIONS

Hirano et al. (Development of a Palpable Carotid Pulse Pressure Sensor Using Electromagnetic Induction, 2012).*
International Search Report of PCT/JP2013/068882.

*Primary Examiner* — Kaylee R Wilson
*Assistant Examiner* — Jay B Shah
(74) *Attorney, Agent, or Firm* — Mattingly & Malur, PC

(57) ABSTRACT

The present invention provides a sphygmomanometer system, including a measurement device pressed against a predetermined part to be measured so that the part to be measured is held down, and a blood pressure measurement device to measure blood pressure based on information from the measurement device. The measurement device includes an average blood pressure detection unit to obtain information on pressure applied to the measurement device, and a blood pressure change amount detection unit to detect a minute change of the part to be measured when the blood pressure change amount detection unit contacts with the part to be measured. The processor of the blood pressure measurement device calculates the average blood pressure, the highest blood pressure, and the lowest blood pressure based on information on pressure obtained from the blood pressure change amount detection unit and the average blood pressure detection unit.

10 Claims, 12 Drawing Sheets

(52) U.S. Cl.
CPC .............. *A61B 5/742* (2013.01); *A61B 5/7405* (2013.01); *A61B 2562/0247* (2013.01); *A61B 2562/04* (2013.01)

(56) References Cited

U.S. PATENT DOCUMENTS

| | | | |
|---|---|---|---|
| 7,306,563 B2* | 12/2007 | Huang | A61B 5/021 600/485 |
| 2002/0105470 A1* | 8/2002 | Kim | G06K 7/10336 343/741 |
| 2005/0171442 A1* | 8/2005 | Shirasaki | A61B 5/021 600/485 |
| 2006/0079791 A1 | 4/2006 | Letremy et al. | |
| 2006/0099559 A1* | 5/2006 | Kohl | A61H 31/007 434/265 |
| 2006/0235311 A1* | 10/2006 | Chan | A61B 5/02141 600/490 |
| 2011/0295128 A1* | 12/2011 | Yuasa | A61B 5/021 600/485 |

FOREIGN PATENT DOCUMENTS

| | | | | |
|---|---|---|---|---|
| JP | H10-211172 A | 8/1998 | | |
| JP | 2000-005139 A | 1/2000 | | |
| JP | 2001-514916 A | 9/2001 | | |
| JP | 2006-519045 A | 8/2006 | | |
| JP | 2006-239114 A | 9/2006 | | |
| JP | WO 2013108361 A1 * | 7/2013 | ............. | A61B 5/021 |
| WO | 03/073932 A1 | 9/2003 | | |
| WO | 2012/054828 A1 | 4/2012 | | |

* cited by examiner

FIG. 9A
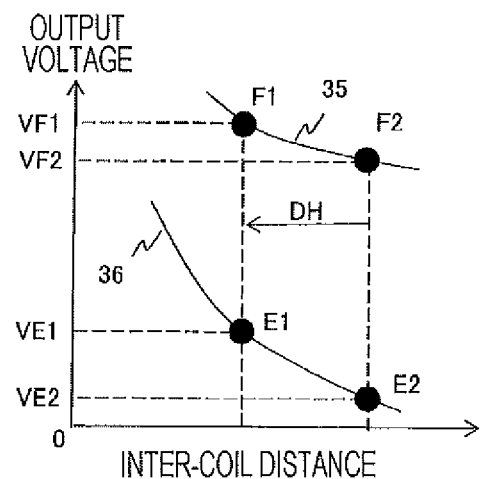
FIG. 9B
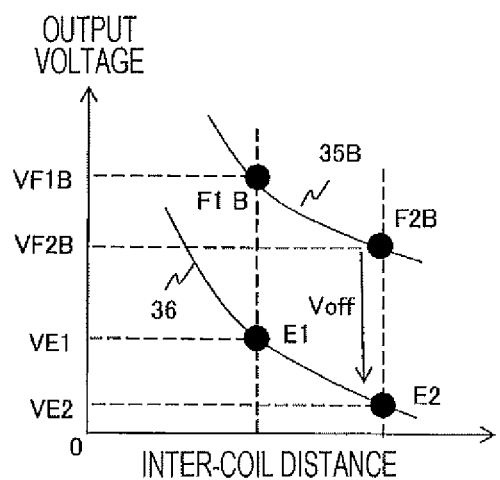
FIG. 9C
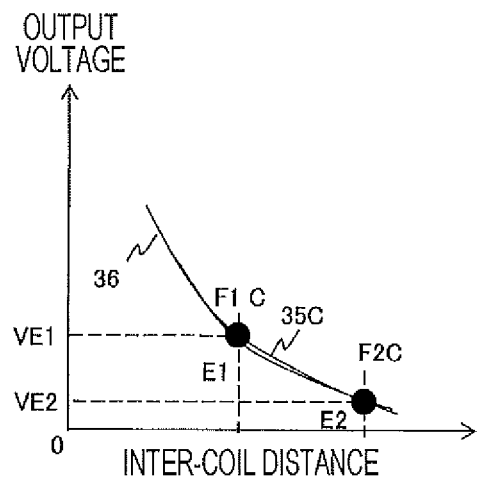

SPHYGMOMANOMETER SYSTEM

TECHNICAL FIELD

The present invention relates to a technology for measuring blood pressure of a subject.

BACKGROUND ART

In sites of emergency medical care for diseases (such as a brain disorder) or accidents (such as a traffic accident), it is of crucial importance to secure blood flow to the brain of a patient. If blood flow to the brain is not sufficient, a patient may have a serious aftereffect in the brain even if his or her life is saved. Whether blood flow to the brain is sufficient or not can be determined on the basis of the strength of pulse (blood pressure) of the carotid artery.

In sites of emergency medical care, blood pressure measurement using a sphygmomanometer cannot be conducted in many cases depending on the circumstances. In such a case, a doctor, an emergency medical technician or the like typically determines whether or not blood flow to the brain of a patient is sufficient by palpating the carotid artery of the patient with fingers.

There is also a device for detecting a pulse wave of the carotid artery of a patient (refer to the Patent Document 1). Note that a pulse wave refers to variation in the volume of body tissues caused by motion of blood in a form of a waveform from the body surface.

Furthermore, the pulse wave can also be measured at the radial artery in the wrist, and there have been increasing needs for quantitative measurement of pulse strength or the like. The palpation of the radial artery has been known as pulse diagnosis in Chinese medicine and has been deemed to allow the holistic health condition to be grasped.

CITATION LIST

Patent Literature

Patent Document 1: Japanese Patent Application Laid-Open No. 10-211172

SUMMARY OF INVENTION

Technical Problem

With the method of palpating the carotid artery of a patient with a finger, however, the determination on whether or not blood flow to the brain of a patient is sufficient varies depending on the persons conducting the palpation, which disadvantageously lacks stability.

Furthermore, Patent Document 1 discloses a technology for determining the presence or absence of a pulse wave in the carotid artery of a patient, but fails to mention determination on whether or not blood flow to the brain of the patient is sufficient when the pulse wave is present.

The present invention has therefore been made in view of the aforementioned circumstances, and an object thereof is stable measurement of blood pressure in a predetermined part to be measured of a subject such as a patient.

Solution to Problem

To achieve the aforementioned object, the present invention provides a sphygmomanometer system for measuring blood pressure of a predetermined part to be measured of a subject, the sphygmomanometer system including: a measurement device pressed against the predetermined part to be measured by a finger of a measurer so that the predetermined part to be measured is held down in measurement of the blood pressure; and a blood pressure measurement device configured to measure the blood pressure according to information from the measurement device, wherein the measurement device includes: a finger holding part configured to hold the finger of the measurer onto the measurement device; a first detection unit configured to obtain information on pressure applied to the predetermined part to be measured via the measurement device by a force of the finger of the measurer held by the finger holding part; and a second detection unit configured to detect a minute change in the predetermined part to be measured due to a pulse when the second detection unit contacts with the predetermined part to be measured together with the first detection unit, and the blood pressure measurement device includes: a processor configured to calculate an average blood pressure according to information on pressure obtained from the first detection unit and calculate a highest blood pressure and a lowest blood pressure according to information on pressure obtained from the second detection unit; and a display unit configured to display a result of calculation of the processor. Other means will be described later.

Advantageous Effects of Invention

The present invention enables stable measurement of blood pressure in a predetermined part to be measured of a subject such as a patient.

BRIEF DESCRIPTION OF DRAWINGS

FIG. 9A is a graph illustrating the relation between an inter-coil distance and output voltage of the measurement device of the embodiment, in which a sensitivity characteristic of each of an average blood pressure P and blood pressure change amount $\Delta P$ is illustrated.

FIG. 9B is a graph illustrating the relation between the inter-coil distance and the output voltage of the measurement device of the embodiment, in which the sensitivity characteristic of the average blood pressure P after sensitivity correction (gain adjustment) thereof and the sensitivity characteristic of the blood pressure change amount ΔP are illustrated.

FIG. 9C is a graph illustrating the relation between the inter-coil distance and the output voltage of the measurement device of the embodiment, in which the sensitivity characteristic of average blood pressure P after sensitivity correction (gain adjustment) and further offset voltage correction thereof and the sensitivity characteristic of the blood pressure change amount ΔP are illustrated.

DESCRIPTION OF EMBODIMENTS

Figure 1:
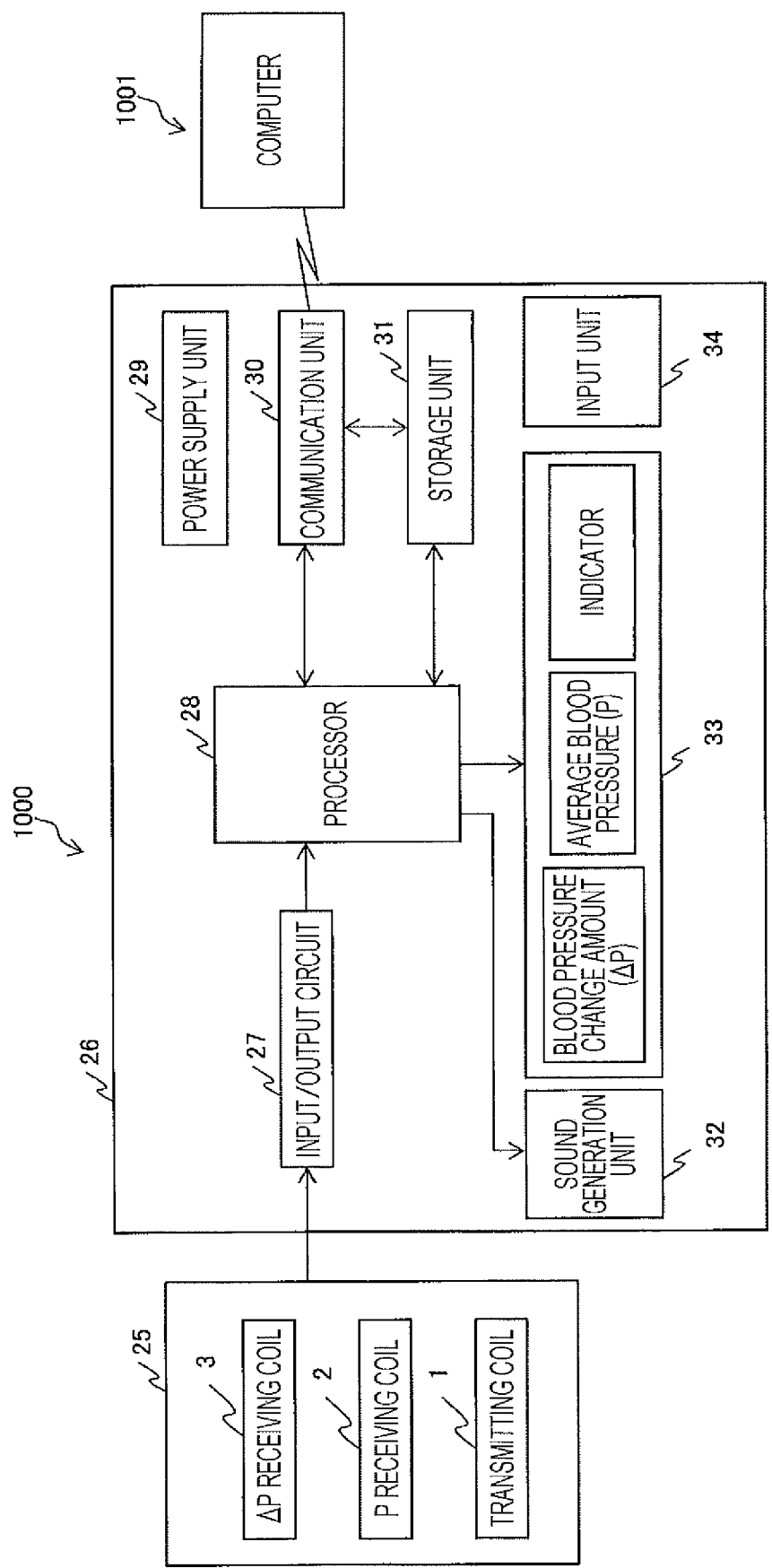
FIG. 1 is a diagram illustrating an overall configuration of a sphygmomanometer system according to an embodiment.

Hereinafter, a mode for carrying out the present invention (hereinafter referred to as "the embodiment") will be described in detail with reference to the drawings where necessary. As illustrated in FIG. 1, a sphygmomanometer system 1000 according to the embodiment is a system for measuring blood pressure in a predetermined part to be measured of a subject, and includes a measurement device 25 and a blood pressure measurement device 26. In FIG. 1, some components of the measurement device 25 are not illustrated as compared to the measurement device 25 in FIG. 2. In the measurement device 25, a transmitting coil 1, a receiving coil 2 for measurement of an average blood pressure (P), and a receiving coil 3 for measurement of a blood pressure change amount (ΔP) are disposed. A detailed structure of the measurement device 25 will be described later with reference to FIG. 2. The receiving coil 2 for measuring an average blood pressure described herein is not a means for accurately measuring the average blood pressure of a subject but refers to a receiving coil for measuring a value near the average blood pressure (a value between highest blood pressure and lowest blood pressure) in an exploratory manner. An accurate average blood pressure is obtained by calculation (which will be described later).

The blood pressure measurement device 26 will now be described. The blood pressure measurement device 26 is a computer device for measuring blood pressure in a part to be measured of a subject on the basis of information from the measurement device 25, and includes an input/output circuit 27, a processor 28, a power supply unit 29, a communication unit 30, a storage unit 31, a sound generation unit 32, a display unit 33, and an input unit 34.

The input/output circuit 27 conveys voltage information received from the receiving coil 2 and the receiving coil 3 of the measurement device 25 to the processor 28. The processor 28 is implemented by, for example, a central processing unit (CPU). The processor 28 calculates pressures applied to the blood pressure change amount detection unit 4 and the average blood pressure detection unit 5 in FIG. 2 on the basis of the voltage information received from the receiving coil 2 and the receiving coil 3 and association information (see FIG. 6) stored in the storage unit 31, and calculates the average blood pressure, the highest blood pressure, and the lowest blood pressure on the basis of the calculation results (details of which will be described later).

The power supply unit 29 is a means for power supply in the blood pressure measurement device 26.

The storage unit 31 is a means for storing various information data, and is implemented by, for example, a random access memory (RAM), a read only memory (ROM), or a hard disk drive (HDD).

The sound generation unit 32 is a means for generating sound, and is constituted by, for example, a loudspeaker. The sound generation unit 32 generates a beep at the start or at the end of measurement with the measurement device 25, and generates sound guidance for a measurer to strengthen or weaken the force pressing the measurement device 25 against apart to be measured, for example (details of which will be described later).

The display unit 33 is a unit for providing various displays, and is constituted by, for example, a liquid crystal display (LCD) or a cathode ray tube (CRT) display device. The display unit 33 displays an indicator or the like visualizing at least one of the blood pressure change amount (ΔP), the average blood pressure (P), the highest blood pressure, and the lowest blood pressure. The input unit 34 is a means operated by a user to input various information data, and is constituted by, for example, a keyboard, a mouse, and the like.

The communication unit 30 communicates with an external computer 1001 (or a communication device) in such a location as an ambulance or a hospital, to transmit data in the sphygmomanometer system 1000 to the computer 1001 and receive control signals for the sphygmomanometer system 1000 from the computer 1001. Examples of the data transmitted from the communication unit 30 to the computer 1001 include measurement data of the average blood pressure (P) and the blood pressure change amount (ΔP) measured by the measurement device 25, and values of the lowest blood pressure, the highest blood pressure, the average blood pressure (P), and the blood pressure change amount (ΔP) calculated by the processor 28 inside the blood pressure measurement device 26 and displayed on the display unit 33. Examples of the contents of the control signals for the sphygmomanometer system 1000 include a timing of data transmission, and a set value for the sphygmomanometer system 1000 (for example, a set value of the strength of the force pressing the measurement device as presented in a flowchart of FIG. 11).

A configuration of the measurement device 25 will now be described with reference to FIG. 2. The measurement device 25 includes a transmitting coil 1 (magnetic field generation unit), a receiving coil 2 (magnetic field detection unit) for measuring the average blood pressure (P), a receiving coil 3 (magnetic field detection unit) for measuring the blood pressure change amount (ΔP), the blood pressure change amount detection unit 4, the average blood pressure detection unit 5, a spring 6 associated with the average blood pressure detection unit 5, a spring 7 associated with the blood pressure change amount detection unit 4, a connector 8 disposed on a substrate of the transmitting coil 1, a holder 9 (finger holding part) and a holding belt 131 for holding the measurement device 25 with a finger, a holding part 10 for holding the entire structure, a lead 111 for connecting the receiving coil 3 to the connector 8 via the substrate of the transmitting coil 1, and a lead 121 for connecting the receiving coil 2 to the connector 8 via the substrate of the transmitting coil 1. Only the average blood pressure detection unit 5 is hatched in FIG. 2 so that the average blood pressure detection unit 5 can be easily distinguished from the blood pressure change amount detection unit 4 and the holding part 10, and there is no other intention of the hatching.

The measurement device 25 is a type of pressure sensor that outputs information on the pressure applied to a part to be measured (a part where the carotid artery of the neck is present, for example) of a subject by the force of a finger of a measurer (such as a doctor) held with the holder 9 and the holding belt 131. More specifically, the measurement device 25 outputs voltage information corresponding to the magnitude of the pressure (details of which will be described later). Although not exactly illustrated in FIG. 2, the transmitting coil 1 is fixed onto a top surface of a part of the holder 9 in the internal space, the holding part 10 and the transmitting coil 1 are fixed to each other, and the transmitting coil 1, the holder 9, and the holding part 10 thus constitute a fixed integral structure, for example.

The receiving coil 3 in a hollow, circular shape is fixed to an upper part of the average blood pressure detection unit 5 and is connected to the holding part 10 via the spring 6. The receiving coil 2 in a circular shape is fixed to an upper part of the blood pressure change amount detection unit 4 and is connected to the average blood pressure detection unit 5 via the spring 7. Although FIG. 2 is drawn as if there are two springs 6 and two springs 7 for convenience sake, it is preferable in terms of cost and operation stability that the spring 6 be constituted by a single coil spring surrounding the average blood pressure detection unit 5 and that the spring 7 be constituted by a single coil spring surrounding the blood pressure change amount detection unit 4, for example.

In order to miniaturize the measurement device 25, the spring 6 and the spring 7 are disposed at positions lower than the receiving coil 2 and the receiving coil 3. This makes a distance D1 (a distance corresponding to the blood pressure change amount $\Delta P$) and a distance D2 (a distance corresponding to an average blood pressure P) smaller (about 2 mm, for example), and enables highly sensitive (high SN) and highly accurate measurement. In addition, since the spring 6 and the spring are substantially in series as described above, the measurement device 25 can be miniaturized (see FIG. 7). In order to accurately measure blood pressure even with the spring 6 and the spring 7 connected in series, the spring 6 has a spring constant larger (harder spring) than that of the spring 7. With the structure described above, when the miniaturized measurement device 25 is pressed at a certain pressure against a part to be measured by a finger, the blood pressure change amount ($\Delta P$) associated with a minutely fluctuating pulse wave can be easily and accurately measured together with the average blood pressure (P).

Figure 3:
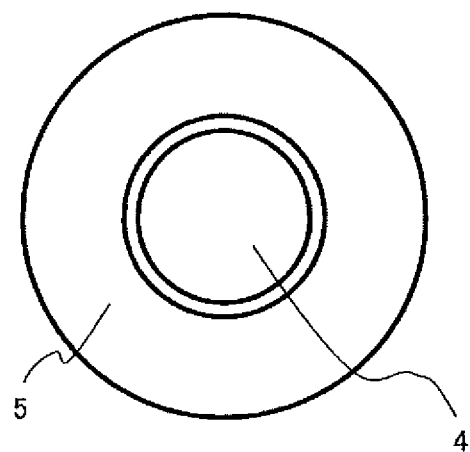
FIG. 3 is a view of an average blood pressure detection unit and a blood pressure change amount detection unit of the measurement device of the embodiment viewed from a bottom surface side.

FIG. 3 illustrates configurations of the blood pressure change amount detection unit 4 and the average blood pressure detection unit 5 viewed from a bottom surface side of the measurement device 25. As illustrated in FIG. 3, the bottom surface side of the measurement device 25 has a concentric configuration in which the average blood pressure detection unit 5 is disposed around the blood pressure change amount detection unit 4. With this configuration, when the measurement device 25 is pressed at a certain pressure (P) against a part to be measured at a position where the blood pressure change amount detection unit 4 contacts with the blood vessel B (see FIG. 8), the average blood pressure detection unit presses the blood vessel B around this position.

Specifically, for palpating the radial artery in the wrist using fingers, for example, the three fingers of forefinger, middle finger, and third finger are typically pressed against the radial artery in the wrist. In this process, the pulse is best felt with the middle finger. This is considered to be because the forefinger and the third finger presses the blood vessel and thus the part of the blood vessel corresponding to the position of the middle finger located between the forefinger and the third finger makes free wall motion. Thus, in the measurement device 25, when the average blood pressure detection unit 5 (corresponding to the forefinger and the third finger) presses the blood vessel B (see FIG. 8), a part therewithin corresponding to the blood pressure change amount detection unit 4 (corresponding to the middle finger) makes free wall motion, allowing a highly accurate measurement of a feeble change in the blood pressure change amount ($\Delta P$). The average blood pressure detection unit 5 therefore has a structure for pressing with a hard spring having a large spring constant, and the blood pressure change amount detection unit 4 has a structure for pressing with a soft spring having a small spring constant.

Figure 4:
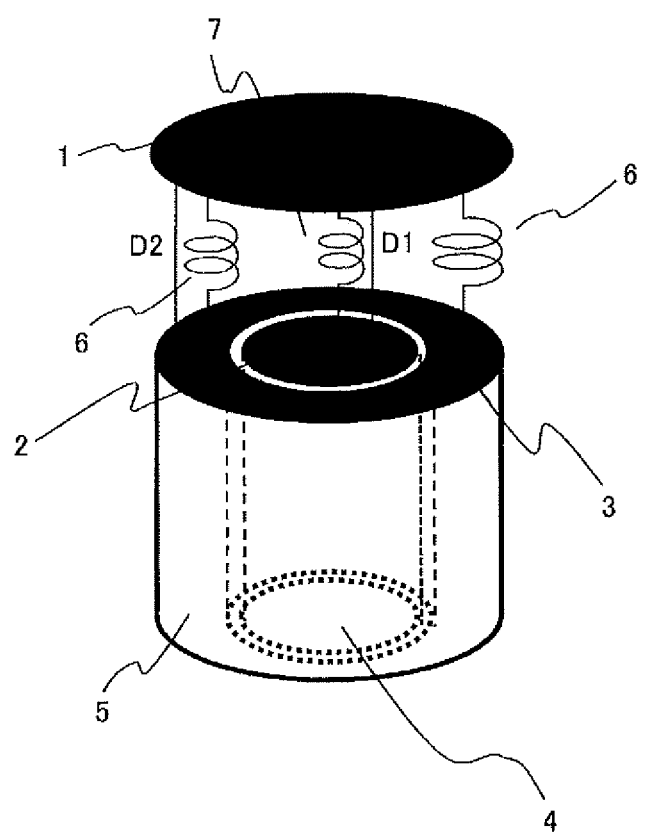
FIG. 4 is a schematic view illustrating a configuration of the average blood pressure detection unit, the blood pressure change amount detection unit, a transmitting coil, a receiving coil, and a spring of the measurement device of the embodiment.

Furthermore, FIG. 4 illustrates a perspective view of a configuration of the blood pressure change amount detection unit 4 and the average blood pressure detection unit 5 (including the spring 6, the spring 7, the transmitting coil 1, the receiving coil 2, and the receiving coil 3). For simplicity of description, the description will be made on the assumption that the spring 6 and the spring 7 are disposed between the transmitting coil 1 and the receiving coils 3 and 2, respectively. Note that the spring 6 and the spring 7 are actually disposed below the receiving coil 3 and the receiving coil 2, respectively, as illustrated in FIG. 2 in order to miniaturize the measurement device 25.

To dispose the blood pressure change amount detection unit 4 and the average blood pressure detection unit 5 concentrically as illustrated in FIG. 3, the transmitting coil 1 and the receiving coil 2 are coils of toggled wiring patterns, and the receiving coil 3 is disposed outside the receiving coil 2. This allows the blood pressure change amount detection unit 4 and the average blood pressure detection unit 5 to move vertically such that the receiving coil 2 and the receiving coil 3 do not contact with each other. As a result of arranging the two receiving coils 2 and 3 at positions within a plane where the receiving coils 2 and 3 are not in contact with each other in this manner, both the distances D1 and D2 can be shortened (about 2 mm, for example), and the transmitting coil 1 is disposed closer to the receiving coil 2 and the receiving coil 3, which achieves higher sensitivity.

Furthermore, as a result of using circular coils for the transmitting coil 1 and the receiving coils 2 and 3, average distances are measured even when the average blood pressure detection unit 5 or the blood pressure change amount detection unit 4 is tilted owing to eccentricity, allowing accurate detection of voltages corresponding to the distance D1 and the distance D2. The concentric configuration (donut-like coil configuration) as described above enables sensitive and accurate measurement. Furthermore, as a result of using a single transmitting coil 1 to transmit a single frequency instead of providing a transmitting coil for each of the receiving coil 2 and the receiving coil 3, the measurement device 25 can be miniaturized and the input/output circuit 27 (see FIGS. 1 and 10) can be simplified.

Figure 5:
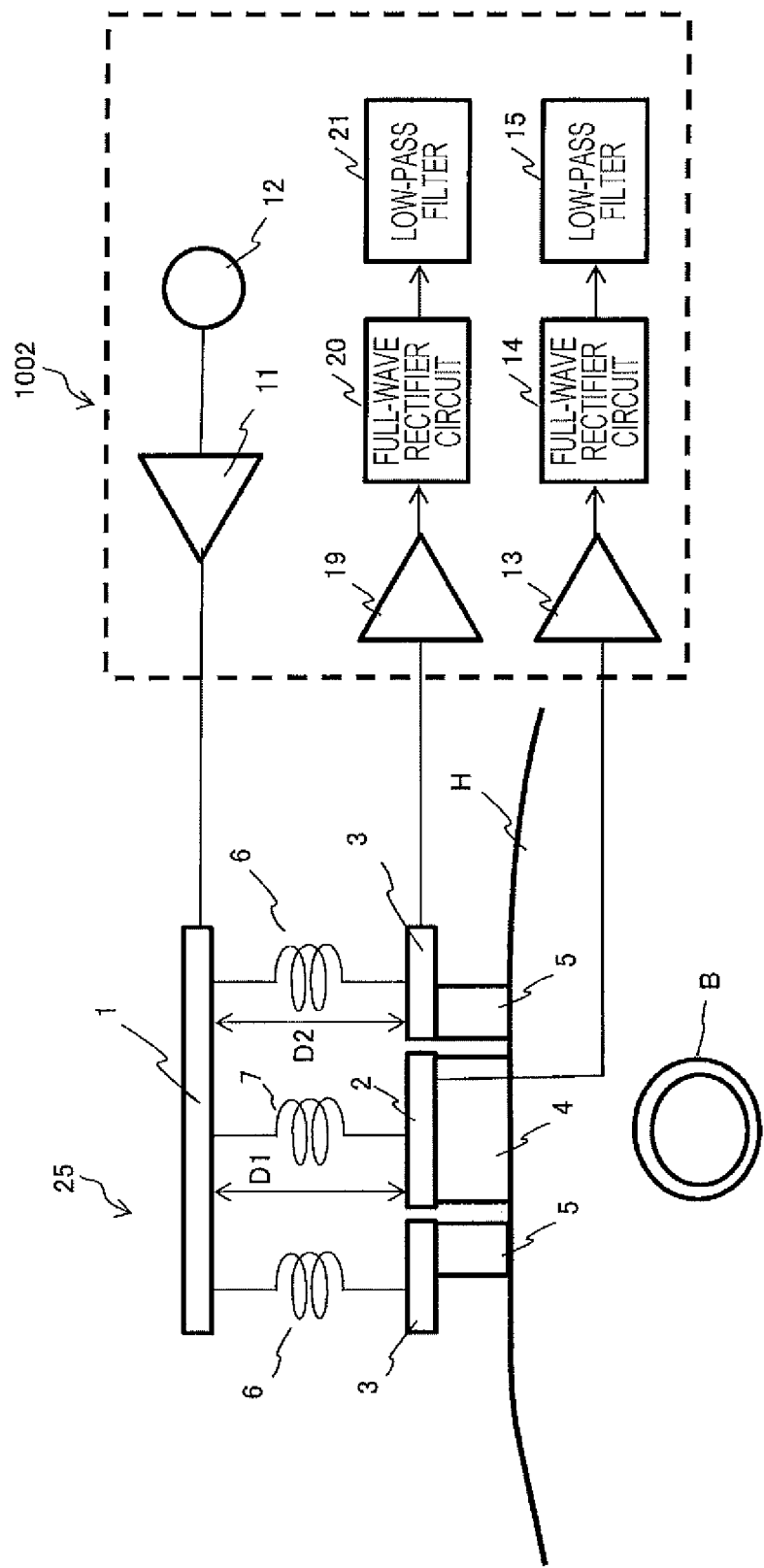
FIG. 5 is a diagram explaining the operating principle of the measurement device of the embodiment.

FIG. 5 illustrates a schematic diagram for explaining the operating principle of the measurement device 25 and a distance measurement circuit 1002. In FIG. 5, similarly to FIG. 4, for simplicity of description, the description will be made on the assumption that the spring 6 and the spring 7 are disposed between the transmitting coil 1 and the receiving coils 3 and 2, respectively. In the measurement device 25, the transmitting coil 1 and the receiving coil 2 are opposed to each other, and the transmitting coil 1 and the receiving coil 3 are opposed to each other.

Note that a human body H has a spring-like property and a damper-like property, and the spring-like property is dominant. The human body H is approximately regarded as a spring having a predetermined spring constant. The spring 6 having a spring constant larger than that of the human body H is selected in advance. In this manner, when a force P is applied to the average blood pressure detection unit 5, the receiving coil 3 (or the receiving coil 2) and the transmitting coil 1 do not contact with each other and, the function of obtaining output voltages depending on the distance D1 and the distance D2 can be maintained.

Next, description will be made on the operation of the measurement device 25 when the measurement device 25 is pressed against a part to be measured of a subject by fingers of a measurer so that the part to be measured is depressed in measurement of the blood pressure of the subject. First, the alternating current oscillator source 12 generates an alternating-current voltage having a specific frequency (20 kHz, for example). The alternating-current voltage is converted into an alternating current having a specific frequency by an amplifier 11, and the alternating current flows into the transmitting coil 1. A magnetic field generated by the alternating current flowing through the transmitting coil 1 generates induced electromotive forces in the receiving coil 2 and the receiving coil 3. Note that the induced electromotive force in the receiving coil 2 is larger as the distance D1 between the receiving coil 2 and the transmitting coil 1 is smaller, and similarly, the induced electromotive force in the receiving coil 3 is larger as the distance D2 between the receiving coil 3 and the transmitting coil 1 is smaller.

The alternating current (having the same frequency as that of the alternating-current voltage generated by the alternating current oscillator source 12) generated in the receiving coil 2 by the induced electromotive force is amplified by a pre-amplifier 13 and the amplified signal is input to the full-wave rectifier circuit 14 (or a detector circuit). The full-wave rectifier circuit 14 rectifies all alternating-current waveforms generated in the receiving coil 2 by the induced electromotive force to be positive waveforms. When the detector circuit is used instead of the full-wave rectifier circuit 14, the amplified signal is detected using a specific frequency or a double frequency generated by the alternating current oscillator source 12. Thus, the output of the alternating current oscillator source 12 is introduced as a reference signal (not illustrated in FIG. 5) to a reference signal input terminal of the detector circuit (not illustrated in FIG. 5). Voltage information (output signal) from the full-wave rectifier circuit 14 (or the detector circuit) passes through a low-pass filter 15 and is then introduced into a difference circuit 16 of the input/output circuit 27 illustrated in FIG. 10.

Similarly, the alternating current (having the same frequency as that of the alternating-current voltage generated by the alternating current oscillator source 12) generated in the receiving coil 3 by the induced electromotive force is amplified by a pre-amplifier 19 and the amplified signal is input to the full-wave rectifier circuit 20 (or a detector circuit). The full-wave rectifier circuit 20 rectifies all alternating-current waveforms generated in the receiving coil 2 by the induced electromotive force to be positive waveforms. When the detector circuit is used instead of the full-wave rectifier circuit 20, the amplified signal is detected using the specific frequency or a double frequency generated by the alternating current oscillator source 12. Thus, the output of the alternating current oscillator source 12 is introduced as a reference signal (not illustrated in FIG. 5) to a reference signal input terminal of the detector circuit (not illustrated in FIG. 5). Voltage information (output signal) from the full-wave rectifier circuit 20 (or the detector circuit) passes through the low-pass filter 21 and is then introduced into an offset/gain adjustment circuit 22 of the input/output circuit 27 illustrated in FIG. 10.

Figure 6:
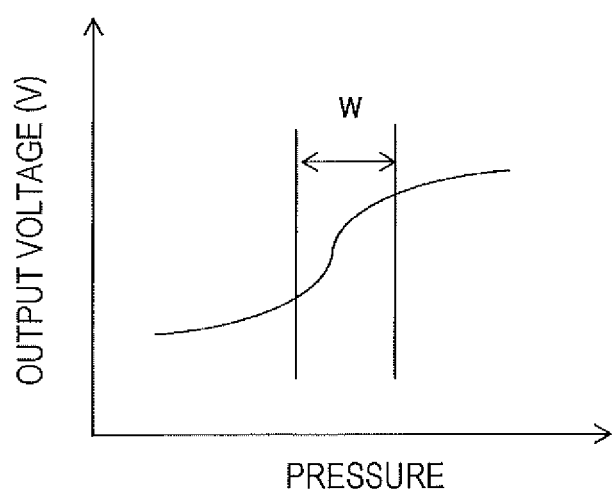
FIG. 6 is a graph illustrating the relation between the pressure and the output voltage of the measurement device of the embodiment.

The relation between the pressure (force ΔP or force P) applied to the blood pressure change amount detection unit 4 or the average blood pressure detection unit 5 (the part to be measured) and the magnitude of the voltage represented by the output signal obtained from the low-pass filter 15 or the low-pass filter 21 is as illustrated in FIG. 6. A range W in FIG. 6 represents a possible range of human blood pressure. Association information illustrated in FIG. 6 indicating the relation between the magnitude of the voltage output by the distance measurement circuit 1002 and the magnitude of the pressure applied to the blood pressure change amount detection unit 4 or the average blood pressure detection unit 5 is stored in advance in the storage unit 31 (see FIG. 1) of the blood pressure measurement device 26 separately for each of the force P and the force ΔP (that is, stored as first association information and second association information). Note that expressing the relation between the output voltage and the pressure illustrated in FIG. 6 by a function using a predetermined function, the least-squares method, or the like improves the accuracy in converting an output voltage into a pressure.

Figure 2:
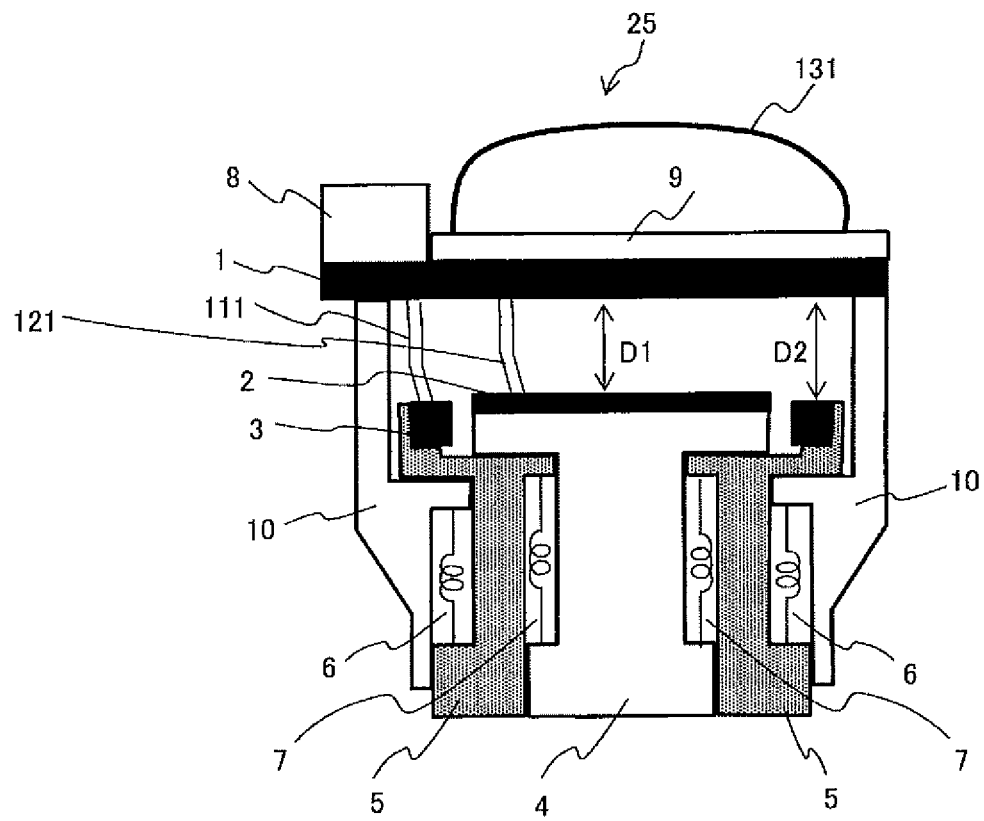
FIG. 2 is a cross-sectional view of a measurement device according to the embodiment.
Figure 7:
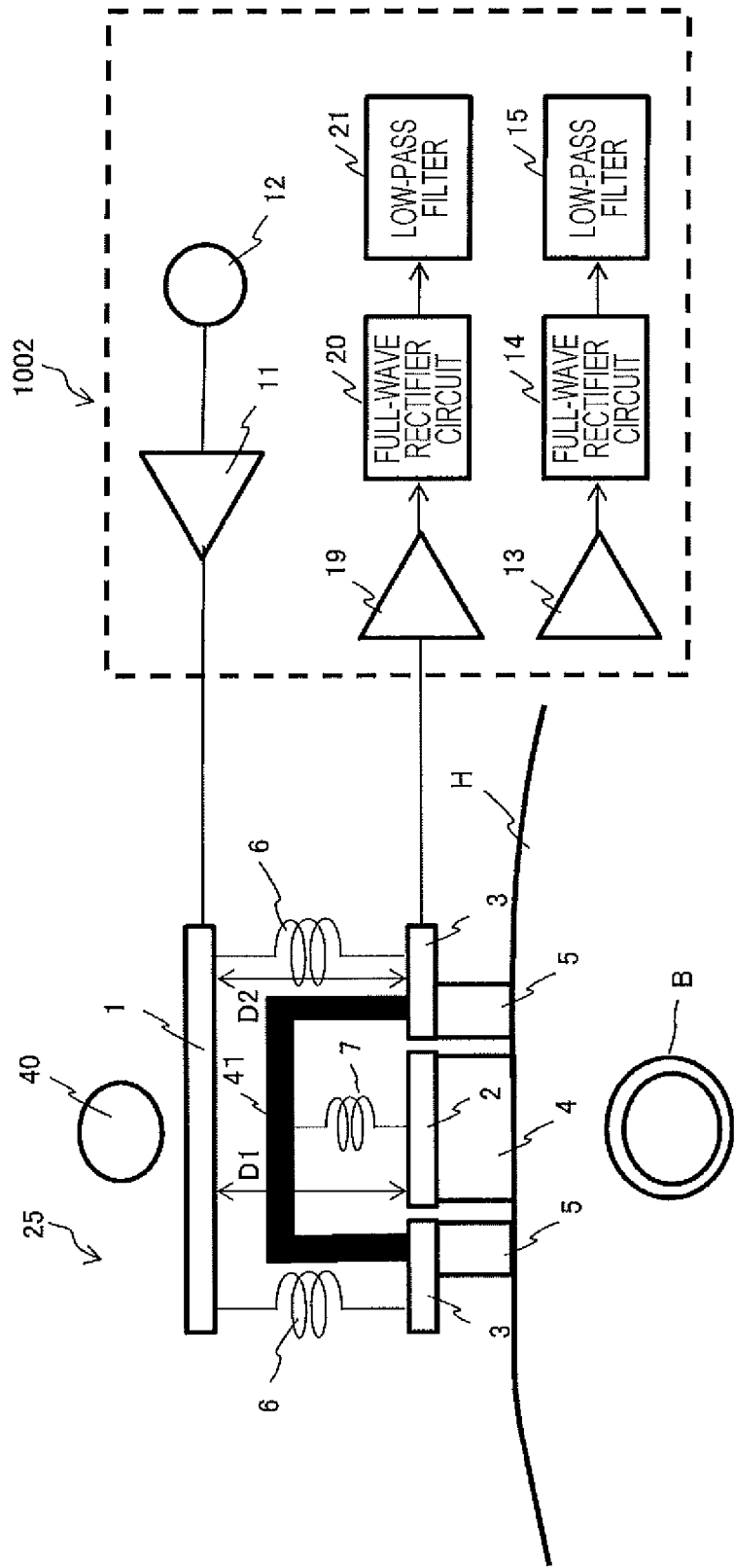
FIG. 7 is a diagram explaining the operating principle of the measurement device of the embodiment in which coils are arranged in series.

FIG. 7 illustrates a schematic diagram for explaining the operating principle of the distance measurement circuit 1002 and the measurement device 25 including a serial connection of the spring 6 and spring 7, the serial connection being employed for miniaturizing the measurement device 25 (the structure illustrated in FIG. 2). The difference from FIG. 5 lies in that the spring 7 is connected between the receiving coil 2 and a fixed part 41 integrated with the receiving coil 3 fixed to the average blood pressure detection unit 5 and that the spring 6 and the spring 7 are connected substantially in series. Since the spring 6 and the spring 7 are connected in series, only the spring 6 is compressed during blood pressure measurement where the measurement device 25 is pressed to the average blood pressure, which allows the spring 7 to be a short spring having such an amount of change that follows minute fluctuation of the blood pressure change amount ΔP and enables further miniaturization of the measurement device 25. Furthermore, the spring 7 with a small spring constant achieves measurement of ΔP with higher accuracy.

Figure 8:
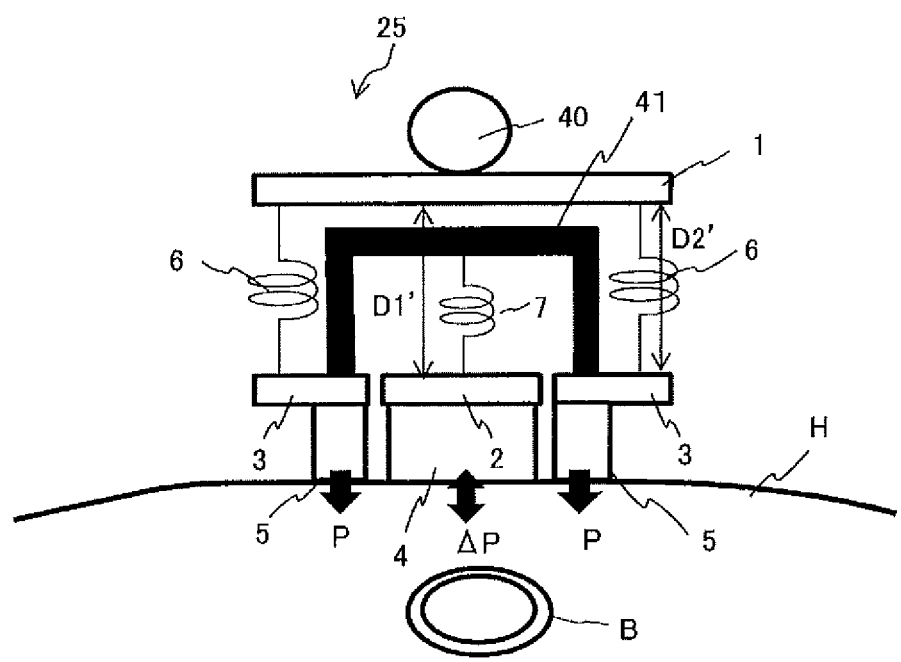
FIG. 8 is a schematic view of operation of the measurement device of the embodiment pressing the blood vessel B.

Next, the operation of the measurement device 25 and the state of a blood vessel (artery) during blood pressure measurement will be described. As illustrated in FIG. 8, when a measurer presses the measurement device 25 against the human body H with the finger 40 with a predetermined force, the force pressing the average blood pressure detection unit 5 against the vicinity of the blood vessel B at a pressure (P) equal to the average blood pressure (including pressures close to the average blood pressure, which also applies below) is balanced with the pressure (P) in the blood vessel B, and thus the wall surface of the blood vessel B makes free wall motion. The balanced pressure P is detected by the average blood pressure detection unit 5, and a pressure (P) equal to the average blood pressure can be detected on the basis of the voltage corresponding to the distance D2. In a state in which the blood vessel B is pressed with the pressure (P) equal to the average blood pressure, vertical motion due to the free wall motion of the blood vessel B appears as pumping of the skin. The blood pressure change amount detection unit 4 follows the pumping of the skin, which changes the distance D1, and a voltage corresponding to the pulse wave can thus be detected.

Next, FIG. 9A illustrates the relation between the inter-coil distance and the output voltage when blood pressure is measured with the configuration illustrated in FIG. 5 or FIG. 7. Since the receiving coil 2 (circular coil) and the receiving coil 3 (donut-shaped coil) have different shapes, the respective relations between the distance D1, the distance D2 and the output voltage (the output of the low-pass filter 15 and the output of the low-pass filter 21) are different from each other as represented by a sensitivity curve 35 of P and a sensitivity curve 36 of ΔP. In contrast, in measurement using the measurement device 25 illustrated in FIG. 8, since the measurement device 25 is pressed up to a certain pressure (pressure close to the average blood pressure), the blood pressure change amount detection unit 4 and the average blood pressure detection unit 5 are compressed by the same distance DH at the same time (see an arrow in FIG. 9A). The compression by the distance DH makes a point F2 on the sensitivity curve 35 of P move to a point F1, and the output voltage thus changes from VF2 to VF1.

On the sensitivity curve 36 of ΔP, a point E2 changes to E1, and the output voltage thus changes from VE2 to VE. The voltage change amounts (VE1−VE2) and (VF1−VF2) measured at E1 and F1, respectively, therefore disadvantageously generate large offset voltages. The easiest method for solving this disadvantage is to provide a high-pass filter in the circuit to cancel the large offset voltages. However, the generation of the large offset voltage causes another disadvantage that the voltage does not readily returns to the base line (zero-bolt line) owing to a time constant that is a reciprocal of the cutoff frequency of the high-pass filter (when the cutoff frequency is 1 Hz, for example, the time constant is one second that is a reciprocal thereof). Furthermore, there is also a disadvantage that the voltage per one bit in analog-to-digital conversion becomes large and detailed voltage cannot be recorded. An easy way to solve the disadvantage of the offset voltage is to obtain a voltage difference between the voltage change amount (VE1−VE2) and the voltage change amount (VF1−VF2) measured at E1 and F1, respectively. In the state of FIG. 9A, however, a large residual voltage remains even after subtraction because of the large voltage difference, and the difference processing is ineffective.

Thus, as illustrated in FIG. 9B, the gain of the output of P is adjusted so that the sensitivity curve 35 of P becomes a curve as represented by a sensitivity curve 35B of P having a slope substantially equal to that of the sensitivity curve 36 to make the voltage change amount (VF1B−VF2B) and the voltage change amount (VE1−VE2) at points F1B and F2B substantially equal to each other. Furthermore, as illustrated in FIG. 9B, the offset voltage Voff is adjusted so that the offset voltage of the sensitivity curve 35B of P and that of the sensitivity curve 36 of ΔP become equal to each other. As illustrated in FIG. 9C, as a result of the adjustment of the offset voltage Voff, the sensitivity curve P becomes a curve as represented by a sensitivity curve 35C, the two outputs become F1C and F2C, and the offset voltage becomes always zero (including substantially zero, which also applies below) as a result of the voltage difference processing even when the inter-coil distance at blood pressure measurement varies from individual to individual.

As a result of conducting the gain correction and the offset voltage correction to correct the sensitivity curve of P and conducting the voltage difference processing as described above, the offset voltage can always be kept at zero even when the inter-coil distance in blood pressure measurement varies from individual to individual, which enables stable measurement with high accuracy. In addition, as a result of storing the relation between the pressure and the voltage output illustrated in FIG. 6 in advance, the conversion from the voltage output to the pressure can be accurately conducted even when the inter-coil distance in blood pressure measurement varies from individual to individual.

Figure 10:
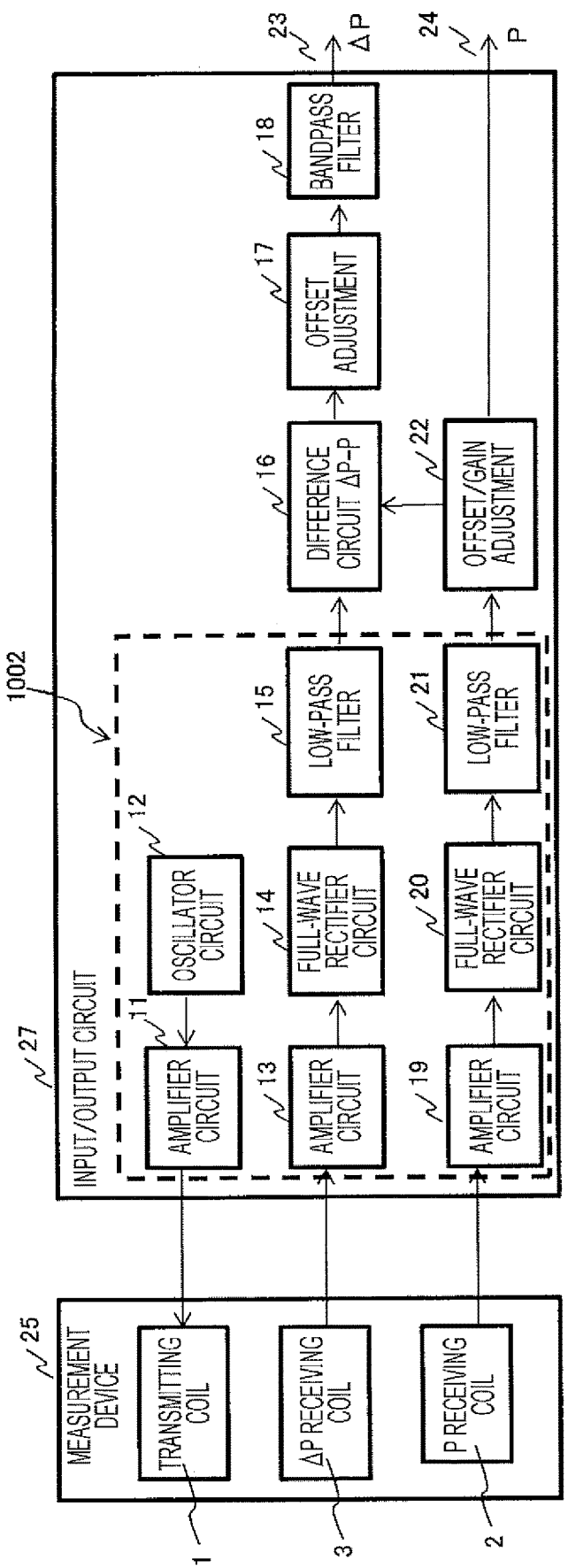
FIG. 10 is a diagram illustrating a configuration of a measurement unit (measurement circuit) and an input/output circuit of the embodiment, and representing a detailed configuration of the input/output circuit.

FIG. 10 illustrates a circuit configuration diagram of the input/output circuit 27 that conducts the processing method including the correction of the sensitivity curve illustrated in FIGS. 9A to 9C. The correction of the sensitivity curve (FIG. 9A, FIG. 9B FIG. 9C) is achieved by the offset/gain adjustment circuit 22, and the voltage difference processing is achieved by the difference circuit 16. The output from the difference circuit 16 passes through an offset adjustment circuit 17 that adjusts the offset of the whole output voltage and the bandpass filter 18 that limits the frequency band to the frequency of the pulse wave, and becomes an output 23 of ΔP. An output 24 of P is the output of the offset/gain adjustment circuit 22 without any changes. As a result of performing the gain correction and the offset voltage correction to correct the sensitivity curve of P and the voltage difference processing on the circuits as described above, an output with no offset voltage can be obtained as the voltage of ΔP. As a result of obtaining the state with no offset voltage in this manner, the resolution per bit in analog-to-digital conversion can be increased, which enables stable measurement with high accuracy.

Next, processing of the blood pressure measurement device 26 will be described with reference to the flowchart of FIG. 11 (also see other drawings where necessary). In step S1, the processor 28 determines whether or not measurement has been started, and proceeds to step S2 if the determination is Yes or returns to step S1 if the determination is No. Specifically, the determination on whether or not the measurement has been started may be made in such a manner that the measurement is determined to have been started when a predetermined operation has been made by the user on the input unit 34 of the blood pressure measurement device 26 or when the output voltage from the receiving coil 2 or the receiving coil 3 has exceeded a predetermined value, or in some other manner.

In step S2, the processor 28 determines whether the force pressing the measurement device 25 is strong, appropriate, or weak. The determination in step S2 may be on the basis of, for example, a predetermined threshold. In order that the strength of the force pressing the measurement device 25 is "appropriate", the pressure applied to at least one of the blood pressure change amount detection unit 4 or the average blood pressure detection unit 5 needs to be within the range W in FIG. 6.

If the force pressing the measurement device 25 is weak ("weak" in step S2), the processor 28 uses the sound generation unit 32 to provide sound guidance in step S3 (step S3), prompting the measurer to press the measurement device 25 harder, and returns to step S2. If the force pressing the measurement device 25 is strong ("strong" in step S2), the processor 28 uses the sound generation unit 32 to provide sound guidance in step S4 (step S4), prompting the measurer to press the measurement device 25 more weakly, and returns to step S2. If the strength of the force pressing the measurement device 25 is appropriate ("appropriate" in step S2), the processor 28 proceeds to step S5.

In step S5, the processor 28 calculates the average blood pressure on the basis of the output 24 from the input/output circuit 27 (see FIG. 10) and the association information on the receiving coil 3 stored in the storage unit 31 (see FIG. 6), and proceeds to step S6. Specifically, a pressure value obtained from the output 24 and the association information on the receiving coil 3 may be set to be the average blood pressure without any changes, or the average blood pressure may be calculated through further predetermined correction, for example. An example of a simple method for correcting the average blood pressure is a method of setting a value of the output 24 maximizing the waveform amplitude (the amplitude value of the pulse wave) of the output 23 to be the average blood pressure. Another example of correcting the average blood pressure is a method of obtaining a first value of the output 24 (for example, 1/10 of the maximum waveform amplitude of the output 23) where the waveform amplitude of the output 23 (the amplitude value of the pulse wave) starts to appear since the pressure applied by the finger is increased starting from 0 and a second value of the output 24 (for example, 1/10 of the maximum waveform amplitude of the output 23) where the waveform amplitude of the output 23 (the amplitude value of the pulse wave) disappears after further application of the pressure by the finger, and setting a midpoint of the first value and the second value as the average blood pressure.

In step S6, the processor 28 calculates the blood pressure change amount ($\Delta P$) on the basis of the output 23 from the input/output circuit 27 (see FIG. 10) and the association information on the receiving coil 2 stored in the storage unit 31 (see FIG. 6), calculates the highest blood pressure and the lowest blood pressure on the basis of the blood pressure change amount ($\Delta P$) and the average blood pressure (P) calculated in step S5, and proceeds to step S7.

In step S7, the processor 28 displays the average blood pressure, the highest blood pressure, and the lowest blood pressure on the display unit 33, and terminates the process. In step S7, an indicator visualizing at least one of the average blood pressure (P), the highest blood pressure, and the lowest blood pressure may also be displayed on the display unit 33.

Figure 12A:
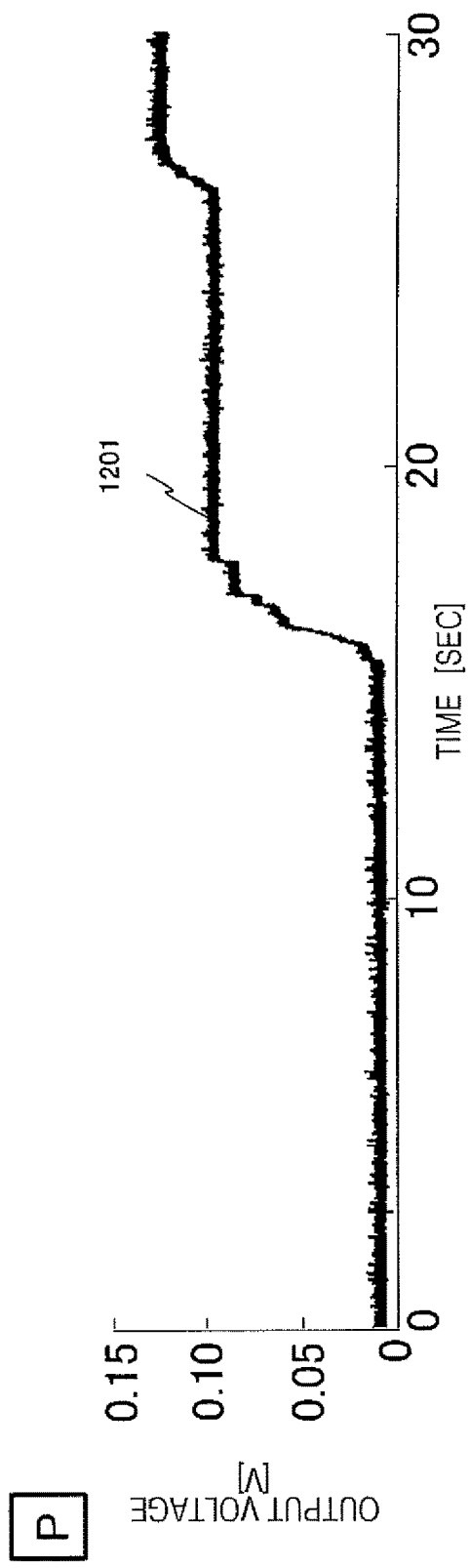
FIG. 12A is a graph illustrating an example of an output voltage waveform (a waveform of an average blood pressure P) in measurement of blood pressure in a carotid artery with the sphygmomanometer system of the embodiment.
Figure 12B:
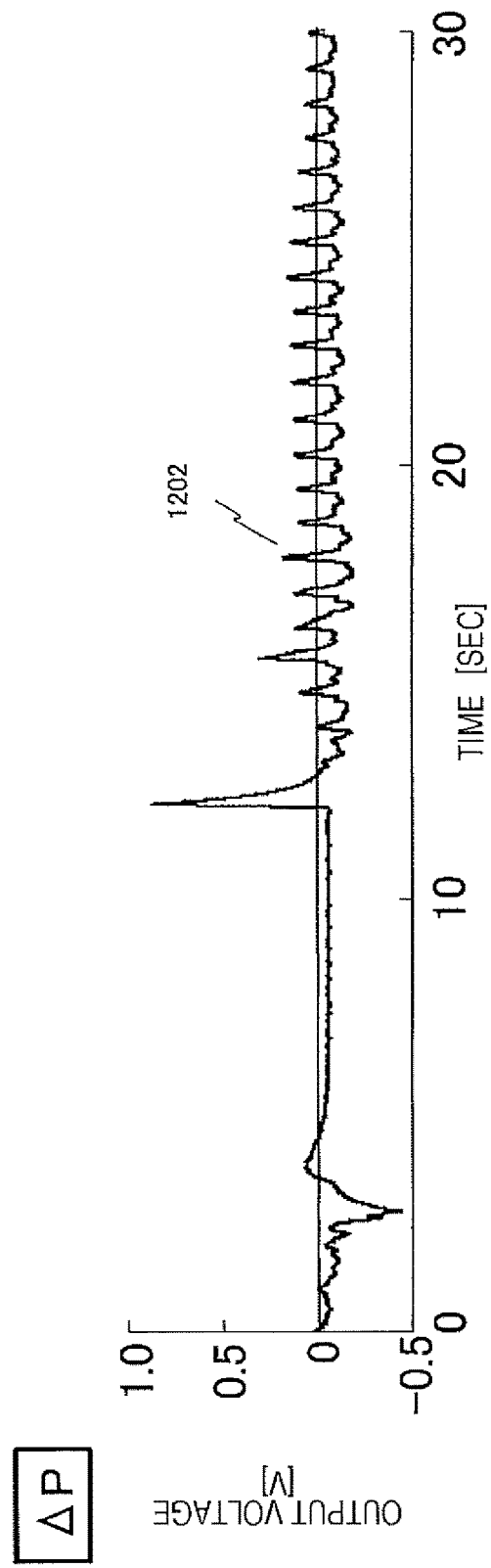
FIG. 12B is a graph illustrating an example of an output voltage waveform (a waveform of a blood pressure change amount ΔP) in measurement of blood pressure in a carotid artery with the sphygmomanometer system of the embodiment.

FIG. 12A and FIG. 12B illustrate examples of the output voltage waveform in measurement of the blood pressure in the carotid artery with the sphygmomanometer system 1000 according to the embodiment. FIG. 12A illustrates an output voltage waveform 1201 of P of the output 24 illustrated in FIG. 10 and FIG. 12B illustrates an output voltage waveform 1202 of $\Delta P$ of the output 23 illustrated in FIG. 10. In measurement of the blood pressure in the carotid artery, since the measurement device 25 is pressed for several seconds until the pressure reaches a value close to the average blood pressure, the value of the output voltage waveform 1201 of P increases correspondingly for several seconds. In the output voltage waveform 1201 of P, a stable part from about 18 seconds to about 27 seconds is the output voltage corresponding to the average blood pressure, and a part from about 27 seconds is the output voltage, when the measurement device 25 is pressed too hard.

In contrast, despite the increase in the value of the output voltage waveform 1201 lasting for several seconds, it can be seen that the output voltage waveform 1202 of $\Delta P$ has no offset corresponding thereto, and that the processing by the offset/gain adjustment circuit 22 (see FIG. 10) and the difference circuit 16 described in the embodiment is therefore very effective. Furthermore, in the output voltage waveform 1202 of $\Delta P$, the pulse wave is clearly measured from about 18 seconds to about 27 seconds, and the calculation of the lowest blood pressure and the highest blood pressure from this waveform can be carried out as below, for example. Note that the voltage generated from 0 to 4 seconds in the output voltage waveform 1202 of $\Delta P$ is an artifact (noise).

$$\text{Average blood pressure } (P) = \text{pressure calculated from voltage of output voltage waveform 1201} \quad (1),\text{ and}$$

$$\text{blood pressure change amount } (\Delta P) = \text{pressure change amount calculated from a differential voltage based on a maximum voltage and a minimum voltage of output voltage waveform 1202} \quad (2).$$

The highest blood pressure and the lowest blood pressure can be calculated as follows using the values calculated by (1) and (2):

$$\text{highest blood pressure} = \text{average blood pressure } (P) + (\Delta P)/2 \quad (3),\text{ and}$$

$$\text{lowest blood pressure} = \text{average blood pressure } (P) - (\Delta P)/2 \quad (4).$$

As described above, according to the sphygmomanometer system 1000 of the embodiment, the measurer (such as a doctor) can press the measurement device 25 held on the finger by the holder 9 and the holding belt 131 against a part to be measured of a subject to know the average blood pressure by means of the average blood pressure detection unit 5 and to obtain the blood pressure change amount (pulse wave fluctuation) by means of the blood pressure change amount detection unit 4, which enables stable measurement of blood pressure at the part to be measured of the subject.

Furthermore, since the measurement device 25 has the configuration in which the springs 6 and 7 are disposed underneath the transmitting coil 1 and the receiving coils 2 and 3 as in FIG. 2, the measurement device 25 is miniaturized such that it can be handled with one hand, attachment and detachment of the measurement device 25 to and from a finger is facilitated, and blood pressure of a part to be measured of a subject can be easily measured in a narrow space such as the inside of an ambulance. Furthermore, since the measurement device 25 is configured to hold a finger by the holder 9 and the holding belt 131 onto the measurement device 25 and to be given a force by the finger, a high operability can be achieved, allowing the measurer to feel the pulse wave with the finger and specify an appropriate part to be measured.

Furthermore, by correcting a sensitivity curve using the offset/gain adjustment circuit 22 with respect to the voltage information detected by the average blood pressure detection unit 5 and by carrying out the voltage difference processing using the difference circuit 16, the offset voltage can always be kept at zero even though the inter-coil distance in blood pressure measurement vary from individual to individual, which enables stable blood pressure measurement with high accuracy.

Furthermore, since the average blood pressure detection unit 5 is disposed in the measurement device 25 and the blood vessel B (see FIG. 8) is pressed moderately at a pressure substantially equal to the average blood pressure, the fluctuation of pulse wave of the part to be measured in contact with the blood pressure change amount detection unit 4 is increased, and the blood pressure can be measured with high accuracy.

Examples of the method for measuring blood pressure can also include a method of converting a displacement on a body surface into an air pressure, but this cannot be expected to have high accuracy owing to personal differences in tissue characteristics such as a blood vessel wall, fat, and skin, noise, and the like such as other sound waves. In contrast, in the embodiment, since the pressure itself caused on the body surface is converted into displacement by the spring 6 and the spring 7, and the displacement is measured in a magnetical manner, the problems of the personal differences in the tissue characteristics and noise hardly arise, and high measurement accuracy can be expected.

Modified Examples

Figure 13A:
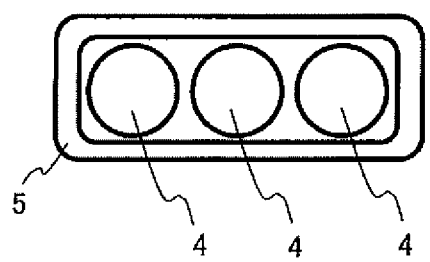
FIG. 13A is a diagram illustrating a modified example of the measurement device of the embodiment.
Figure 13B:
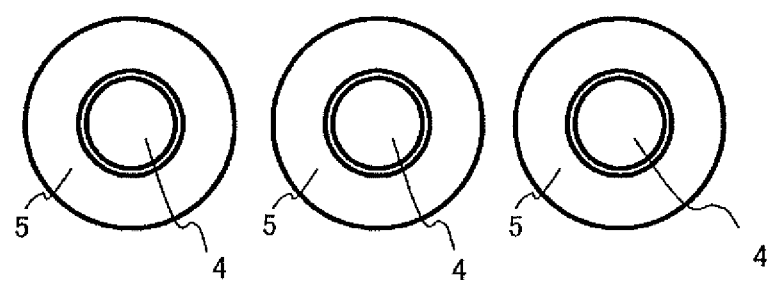
FIG. 13B is a diagram illustrating a modified example of the measurement device of the embodiment.
Figure 13C:
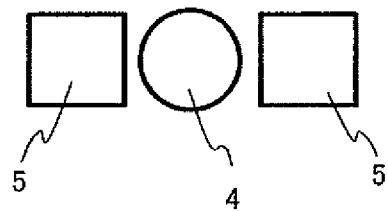
FIG. 13C is a diagram illustrating a modified example of the measurement device of the embodiment.

Next, modified examples of the measurement device 25 will be described with reference to FIGS. 13A to 13C. In FIGS. 13A to 13C, only the numbers and the relative positions of the blood pressure change amount detection unit 4 and the average blood pressure detection unit 5 are presented.

As illustrated in FIG. 13A, in the measurement device 25 of this modified example, three blood pressure change amount detection units 4 are provided, and the average blood pressure detection unit 5 is disposed to surround the blood pressure change amount detection units 4. As a result of providing a plurality of blood pressure change amount detection units 4 in this manner, blood pressure measurement with higher flexibility and higher accuracy can be conducted by using an average of voltages from three blood pressure change amount detection units 4 or by using voltage information with the highest value of the voltage values of three blood pressure change amount detection units 4. Alternatively, a voltage from each of three blood pressure change amount detection units 4 can be detected and applied to pulse diagnosis of the radial artery in a wrist to be measured by three fingers as carried out in Chinese medicine.

Next, as illustrated in FIG. 13B, in a measurement device 25 of this modified example, three sets of the blood pressure change amount detection unit 4 and the average blood pressure detection unit 5 are provided. As a result of using a plurality of sets of the blood pressure change amount detection unit 4 and the average blood pressure detection unit 5 in this manner, measurement can be conducted at a plurality of parts at the same time, which enables blood pressure measurement with higher flexibility and higher accuracy. Similarly to FIG. 13A, the configuration of FIG. 13B can also be applied to pulse diagnosis of the radial artery in a wrist to be measured by three fingers as carried out in Chinese medicine.

Next, as illustrated in FIG. 13C, in a measurement device of this modified example, two average blood pressure detection units 5 are provided, in which one of the average blood pressure detection units 5, the blood pressure change amount detection unit 4, and the other of the average blood pressure detection units 5 are aligned in this order. With this arrangement, blood pressure measurement can also be conducted even in a case where blood pressure is measured on a part such as the radial artery in a wrist, which can only be pressed in a thin area owing to the presence of a tendon and the like nearby.

Similarly to FIG. 13A, the configuration of FIG. 13C can also be applied to pulse diagnosis of the radial artery in a wrist to be measured by three fingers as carried out in Chinese medicine. The configuration illustrated in FIG. 13C in which the blood pressure change amount detection unit 4 is disposed between two average blood pressure detection units 5 independent of each other, however, is disadvantageous in that a case where the blood vessel B cannot be pressed sufficiently by the average blood pressure detection unit 5 (the average blood pressure detection unit 5 is shifted from the position of the blood vessel B) owing to the orientation of the measurement device 25 is likely to occur. The arrangement of the blood pressure change amount detection unit 4 and the average blood pressure detection unit 5 in a concentric manner as illustrated in FIG. 3 is therefore an optimum arrangement.

The present embodiment has been described as above, but the mode of the present invention is not limited thereto. For example, a substantially cylindrical member having a finger sac shape may be used to hold a finger on the measurement device 25 instead of the holder 9 and the holding belt 131. In this manner, the finger is less likely to be separated from the measurement device 25 and thus more stable blood pressure measurement is achieved.

Furthermore, data may be encrypted in data transmission from the measurement device 25 to the blood pressure measurement device 26 and data transmission from the blood pressure measurement device 26 to the computer 1001. Furthermore, data transmission from the measurement device 25 to the blood pressure measurement device 26 may be carried out wirelessly.

Figure 11:
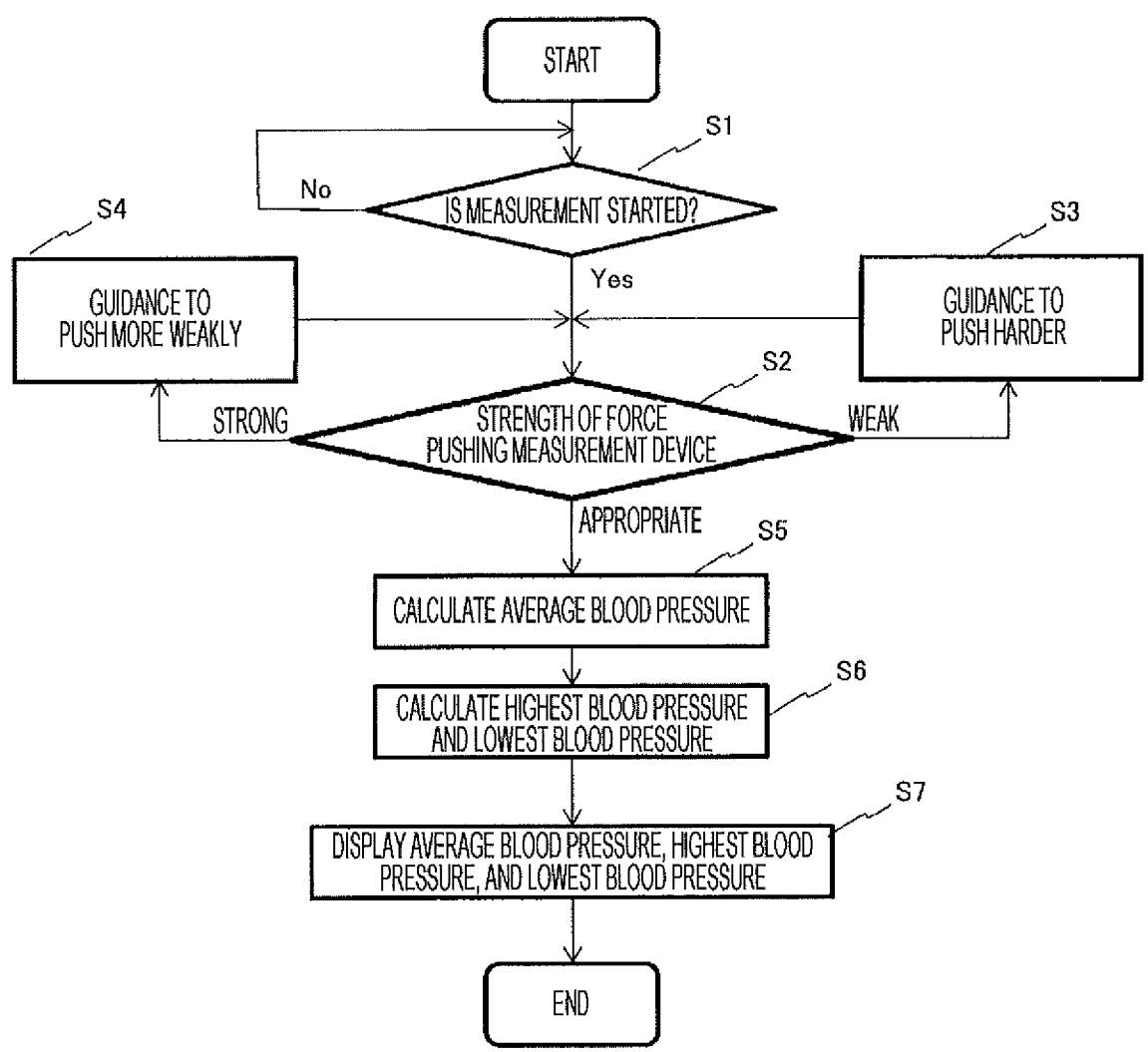
FIG. 11 is a flowchart illustrating a flow of processes performed by the blood pressure measurement device of the embodiment.

Furthermore, as a modified example of steps S2 to S5 in the flowchart of FIG. 11, the average blood pressure may be tentatively calculated in step S2, the sound generation unit 32 may be used to repeat sound guidance to the measurer to strengthen or weaken the force pressing the measurement device 25 onto the part to be measured until the tentatively calculated value of the average blood pressure does not become larger any more, and the tentatively calculated value of the average blood pressure that is determined to be maximum may be determined to be the average blood pressure.

Furthermore, for example, although the blood pressure change amount detection unit 4 and the average blood pressure detection unit 5 are illustrated to be integrated members in FIG. 2, the blood pressure change amount detection unit 4 and the average blood pressure detection unit 5 may have a structure in which the two members are screwed to each other for convenience of assembly with the springs 6 and 7 and the like.

When the bottom surface side of the average blood pressure detection unit 5 has a circular shape, the outer diameter is preferably 20 mm or smaller for measurement of a carotid artery, and 3 mm or smaller for measurement of a radial artery of a wrist, and the sizes of the measurement device 25 and the like are preferably adjusted according thereto. Other specific configurations and processes can be modified where appropriate without departing from the scope of the present invention.

REFERENCE SIGNS LIST

1 transmitting coil
2 receiving coil (first detection unit; first magnetic field detection unit; first receiving coil)
3 receiving coil (second detection unit; second magnetic field detection unit; second receiving coil)

4 blood pressure change amount detection unit
5 average blood pressure detection unit
6 spring (first spring)
7 spring (second spring)
8 connector
9 holder
10 holding part
11 amplifier
12 alternating current oscillator source
13 pre-amplifier
14 full-wave rectifier circuit
15 low-pass filter
16 difference circuit (difference processing unit)
17 offset adjustment circuit
18 bandpass filter
19 pre-amplifier
20 full-wave rectifier circuit
21 low-pass filter
22 offset/gain adjustment circuit (offset/gain adjustment unit)
23 output ($\Delta P$)
24 output (P)
25 measurement device
26 blood pressure measurement device
27 input/output circuit
28 processor
29 power supply unit
30 communication unit
31 storage unit
32 sound generation unit
33 display unit
34 input unit
35 sensitivity curve of P
36 sensitivity curve of $\Delta P$
40 finger
41 fixed part
111 lead
121 lead
131 holding belt
1000 sphygmomanometer system
1001 computer
1002 distance measurement circuit
1201 output voltage waveform of P of output 23
1202 output voltage waveform of $\Delta P$ of output 24
B blood vessel
H human body
D1, D2, DH distance
Voff offset voltage
VF1, VF2, VF1B, VF2B, VE1, VE2 voltage
E1, E2, F1, F2, F1B, F2B, F1C, F2C measurement points

The invention claimed is:

1. A sphygmomanometer system for measuring blood pressure of a predetermined part of a subject, the sphygmomanometer system comprising:
a first device configured to be pressed against the predetermined part of the subject by a force of a finger of a measurer and to generate a plurality of voltage signals in measurement of the blood pressure; and
a second device configured to measure the blood pressure according to the plurality of voltage signals from the first device,
wherein the first device includes:
a holder;
a transmission coil fixed relative to the holder and configured to generate a magnetic field;
a first detector configured to be pressed against the predetermined part and to move relative to the transmission coil;
a first spring which connects the first detector to the holder and configured to repel the first detector;
a first reception coil disposed on the first detector;
a second detector supported by the first detector and configured to be pressed against the predetermined part and to move relative to the transmission coil;
a second spring which connects the first detector and the second detector and is configured to repel the second detector, the second spring having a spring constant smaller than that of the first spring; and
a second reception coil disposed on the second detector,
wherein the first device is configured to output a first voltage signal corresponding to movement between the transmission coil and the first reception coil on the first detector and output a second voltage signal corresponding to movement between the transmission coil and the second reception coil on the second detector, and
wherein the second device includes:
a display; and
a processor configured to:
calculate an average blood pressure based on the first voltage signal and calculate a highest blood pressure and a lowest blood pressure based on the second voltage signal and the average blood pressure; and
display the average blood pressure, the highest blood pressure and the lowest blood pressure.

2. The sphygmomanometer system according to claim 1, wherein the second device further includes a storage device configured to store first association information indicating a relation between a magnitude of the first voltage signal and a magnitude of the pressure applied to the first detector from the predetermined part of the subject and second association information indicating a relation between a magnitude of the second voltage signal and a magnitude of the pressure applied to the second detector from the predetermined part of the subject, and
wherein the processor is further configured to calculate the average blood pressure according to the first voltage signal and the first association information, and calculate the highest blood pressure and the lowest blood pressure according to the average blood pressure, the second voltage signal, and the second association information.

3. The sphygmomanometer system according to claim 1, wherein the second device further includes a speaker, and
wherein the processor is further configured to:
output sound guidance to the measurer to strengthen or weaken the force pressing the holder against the predetermined part while the average blood pressure increases, and display the average blood pressure on the display when the average blood pressure is determined to be a maximum.

4. The sphygmomanometer system according to claim 1, wherein the first receiving coil has a circular shape, the second receiving coil has a circular shape, and the first receiving coil is disposed around the second receiving coil so that the first receiving coil and the second receiving coil do not contact with each other within a plane in a direction of vertical motion of the first detector and the second detector.

5. The sphygmomanometer system according to claim 1, wherein the second device further includes:

an offset/gain adjustment circuit configured to adjust a first sensitivity characteristic curve of the movement between the transmission coil and the first reception coil to correspond to a second sensitivity characteristic curve of the movement between the transmission coil and the second reception coil, and wherein the average blood pressure is calculated based on the first voltage signal and the adjustment to the first sensitivity characteristic curve.

6. The sphygmomanometer system according to claim 1, wherein the holder has a cylindrical shape to hold the finger of the measurer.

7. The sphygmomanometer system according to claim 2, wherein the second device further includes a speaker, and wherein the processor is further configured to:

output sound guidance to the measurer to strengthen or weaken the force pressing the holder against the predetermined part while the average blood pressure increases, and display the average blood pressure on the display when the average blood pressure is determined to be a maximum.

8. The sphygmomanometer system according to claim 1, wherein the first spring is configured to repel the first detector away from the transmission coil, and the second spring is configured to repel the second detector away from the transmission coil.

9. The sphygmomanometer system according to claim 1, wherein the first coil is disposed on the first detector and the second coil is disposed on the second detector and the second coil is configured to move separately from the first coil without contacting the first coil.

10. The sphygmomanometer system according to claim 1, wherein the second detector is configured to move separately from the first detector.

* * * * *